(12) United States Patent  (10) Patent No.: US 8,043,240 B2
Piatek  (45) Date of Patent: Oct. 25, 2011

(54) CAST COVER

(75) Inventor: Lee J. Piatek, Caucos, CA (US)

(73) Assignee: Lee J. Piatek, Cayucos, CA (US)

( * ) Notice: Subject to any disclaimer, the term of this patent is extended or adjusted under 35 U.S.C. 154(b) by 446 days.

(21) Appl. No.: 12/315,503

(22) Filed: Dec. 3, 2008

(65) Prior Publication Data

US 2009/0149786 A1 Jun. 11, 2009

Related U.S. Application Data

(60) Provisional application No. 61/005,319, filed on Dec. 4, 2007.

(51) Int. Cl.
A61F 5/00 (2006.01)
(52) U.S. Cl. .............................. 602/3; 602/1
(58) Field of Classification Search ............... 602/1, 3, 602/8, 12, 36, 21, 63, 64, 62, 75, 20; 128/856, 128/878, 879–880; 2/16, 22, 455; 36/110; 119/850; D24/190
See application file for complete search history.

(56) References Cited

U.S. PATENT DOCUMENTS

| 3,741,203 | A | * | 6/1973 | Liman | 602/3 |
| 4,530,350 | A | * | 7/1985 | Brown et al. | 602/3 |
| 2008/0195009 | A1 | * | 8/2008 | Satkowiak | 602/3 |

OTHER PUBLICATIONS

Unknown, "Padding & Protectives", Cramer Sports Med, Copyright 2004 Cramer Products, Inc., http://www.cramersportsmed.com/products, Nov. 6, 2007, U.S.A.

* cited by examiner

Primary Examiner — Patricia Bianco
Assistant Examiner — Ophelia Hawthorne
(74) Attorney, Agent, or Firm — Baker & Hostetler LLP

(57) ABSTRACT

A protective cover for a cast. Exemplary embodiments include a cover for a lower arm cast including an optional thumb cover. Exemplary embodiments may be constructed from resilient foam located within a protective shell, and the protective shell may include fasteners arranged to retain the cast cover around the cast. An exemplary thumb cover includes a plurality of pockets, each of which holds a thumb pad. The exemplary thumb cover may be installed on the cast prior to installing the cast cover, and the thumb cover may extend through an opening in the cast cover.

12 Claims, 9 Drawing Sheets

CAST COVER

CROSS REFERENCE TO RELATED APPLICATION

This application claims the benefit of U.S. Provisional Application No. 61/005,319, filed Dec. 4, 2007, which is incorporated by reference.

BACKGROUND

This disclosure pertains to a protective cover for a cast and, more particularly, a protective cover for a cast including a resilient core.

In some circumstances, an individual wearing a cast may desire to participate in an activity, such as an athletic activity, during which the cast is covered. In particular, some athletic organizations require casts to be covered during sporting events.

SUMMARY

Exemplary embodiments include a protective cover for a cast, such as a cover for a lower arm cast including an optional thumb cover. Exemplary embodiments may be constructed from resilient foam located within a protective shell, and the protective shell may include fasteners arranged to retain the cast cover around the cast. An exemplary thumb cover includes a plurality of pockets, each of which holds a thumb pad. The exemplary thumb cover may be installed on the cast prior to installing the cast cover, and the thumb cover may extend through an opening in the cast cover.

In an aspect, a protective cover for a cast may include a core constructed of flexible and elastic foam sized to at least partially cover a cast; an outer shell including a portion sized to receive the core such that the core is substantially covered by the shell; and a plurality of fasteners attached to the outer shell and arranged to retain the outer shell about the cast.

In a detailed embodiment, the cast may include a splint.

In detailed embodiment, the cover may include a thumb cover at least partially covering an extending thumb portion of the cast. In a further detailed embodiment, the thumb cover may include a thumb cover shell and at least one thumb pad received with at least one pocket within the thumb cover shell.

In detailed embodiment, the outer shell may include a first opening and the core includes a second opening, and the first opening and the second opening may be aligned. In a further detailed embodiment, the cover may include a thumb cover, and the thumb cover may extend through the first opening and the second opening.

In detailed embodiment, the plurality of fasteners may include at least one hook and loop fastener.

In another aspect, a wearable article may include a cast cover including a substantially planar, resilient core including at least one opening extending therethrough, a cast cover shell sized to receive the core and including at least one opening aligned with the opening in the core, and at least one cast cover fastener coupled to the shell and arranged to retain the shell at least partially around an arm portion of a cast; and a thumb cover including a thumb cover shell including a plurality of thumb cover pockets, a plurality of resilient thumb pads respectively received within the plurality of thumb cover pockets, and at least one thumb cover fastener coupled to the thumb cover and arranged to retain the thumb cover at least partially around a thumb portion of the cast.

In a detailed embodiment, at least a portion of the thumb cover may extend through the opening in the core and the opening in the arm cover shell.

In detailed embodiment, the thumb cover may include two flaps arranged to extend around a wrist portion of the cast. In a further detailed embodiment, the flaps may include corresponding hook and loop closure portions arranged to couple the flaps together around the wrist portion of the cast.

In a detailed embodiment, the at least one cast cover fastener may include a hook and loop fastener.

In detailed embodiment, the at least one thumb cover fastener may include a hook and loop fastener.

In another aspect, a method for applying a protective cover for a cast may include arranging a cast cover at least partially around a cast, the cast cover including an outer shell, a resilient core received within the outer shell, and a cast cover fastener; and securing the cast cover in place around the cast by coupling the cast cover fastener.

In a detailed embodiment, the method may include installing a thumb cover over a thumb portion of the cast. In a detailed embodiment, the step of installing the thumb cover may be performed prior to the step of arranging the cast cover around the cast, and the step of arranging the cast cover around the cast may include placing the thumb cover through an opening in the cast cover.

In a detailed embodiment, the step of installing the thumb cover may be performed after the step of arranging the cast cover around the cast, and the step of installing the thumb cover may include affixing the thumb cover to the cast cover.

In a detailed embodiment, the step of arranging the cast cover around the cast may include inserting the resilient core into the outer shell through an opening edge. In a further detailed embodiment, the step of inserting the resilient core into the outer shell may include securing the opening edge using at least one fastening device.

BRIEF DESCRIPTION OF THE DRAWINGS

The detailed description refers to the following figures in which.

DETAILED DESCRIPTION

An exemplary cast cover may be used to cover a short arm cast, such as the type used to immobilize a wrist fracture, for example. The cast cover may be used by an athlete who desires to participate in an athletic contest while wearing a cast, for example.

Figure 1:
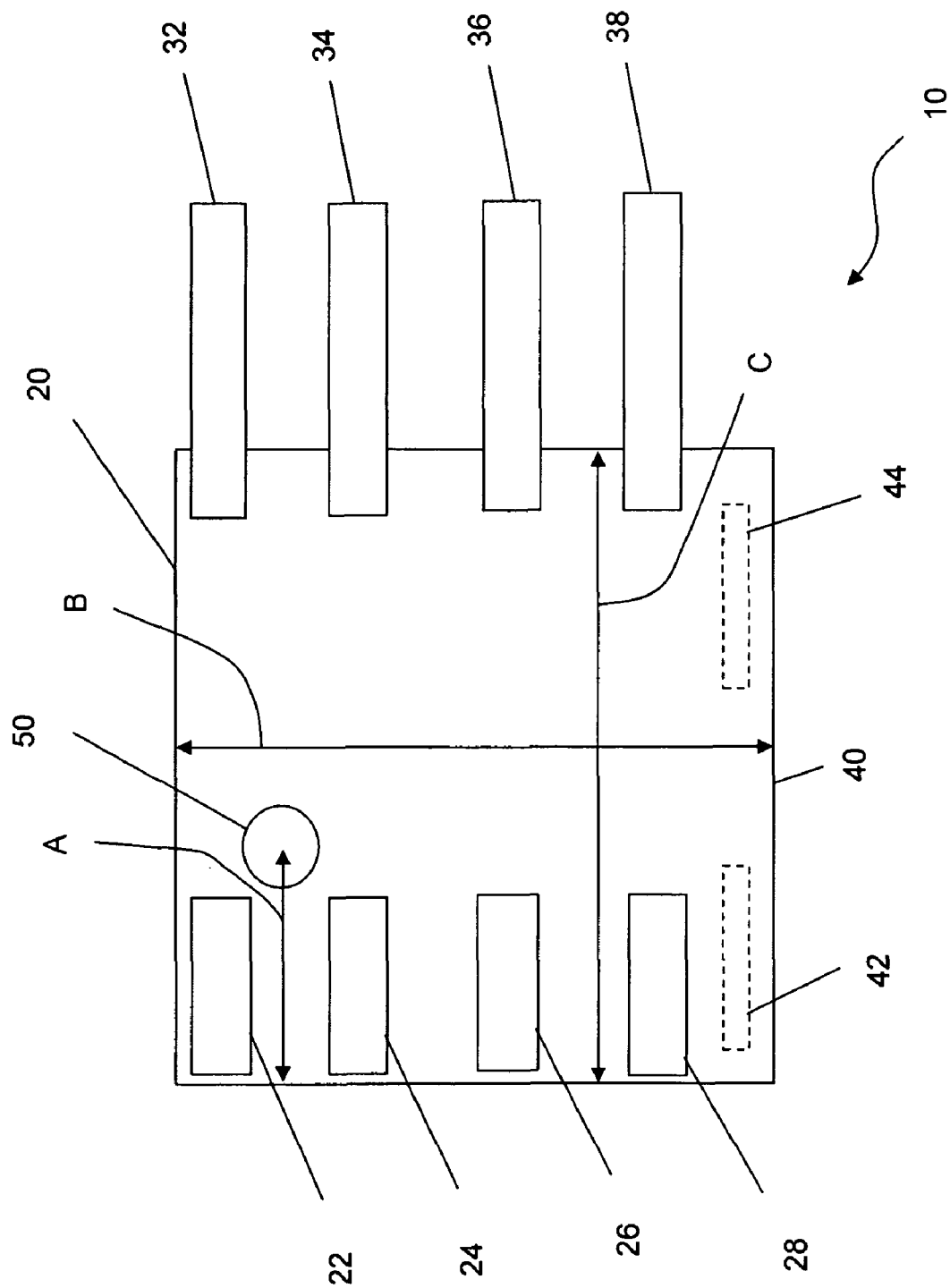
FIG. 1 is a plan view of an exemplary cast cover.
Figure 2:
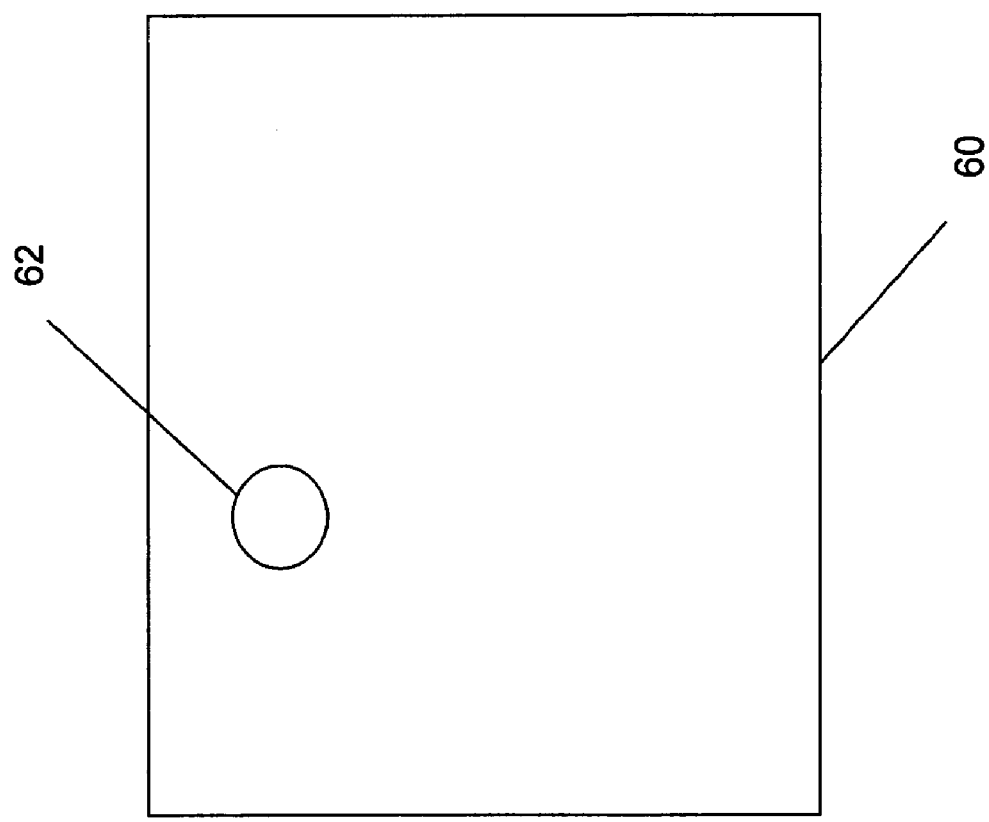
FIG. 2 is a plan view of an exemplary core.

As shown in FIGS. 1 and 2, an exemplary cast cover 10 may include a shell 20. The shell 20 may be adapted to be secured around a cast worn by a user. The shell 20 may include an opening 50 adapted to allow a body part to extend therethrough. For example and without limitation, the opening 50 may be adapted to allow a user to extend a thumb 6 through opening 50 when the cast cover 10 is worn over the user's forearm 2 and a cast 4 (see, e.g., FIG. 3).

In an exemplary embodiment, the shell 20 may generally be in the form of a flat pocket having an opening edge 40. The opening edge 40 may be secured (shut) using at least one fastening device such as, but not limited to, one or more sets of hook and loop closures. In the exemplary embodiment depicted in FIG. 1, stitching lines 42, 44 indicate where hook and loop fasteners are sewn within the pocket proximate to the opening edge 40. Other embodiments may include one or more openings at alternative positions on the shell, such as on a side or on a different edge. Further, the opening may not include a fastening device in some embodiments. In such an embodiment, the shape and/or size of the opening may be adapted to retain objects located within the shell 20.

Figure 3:
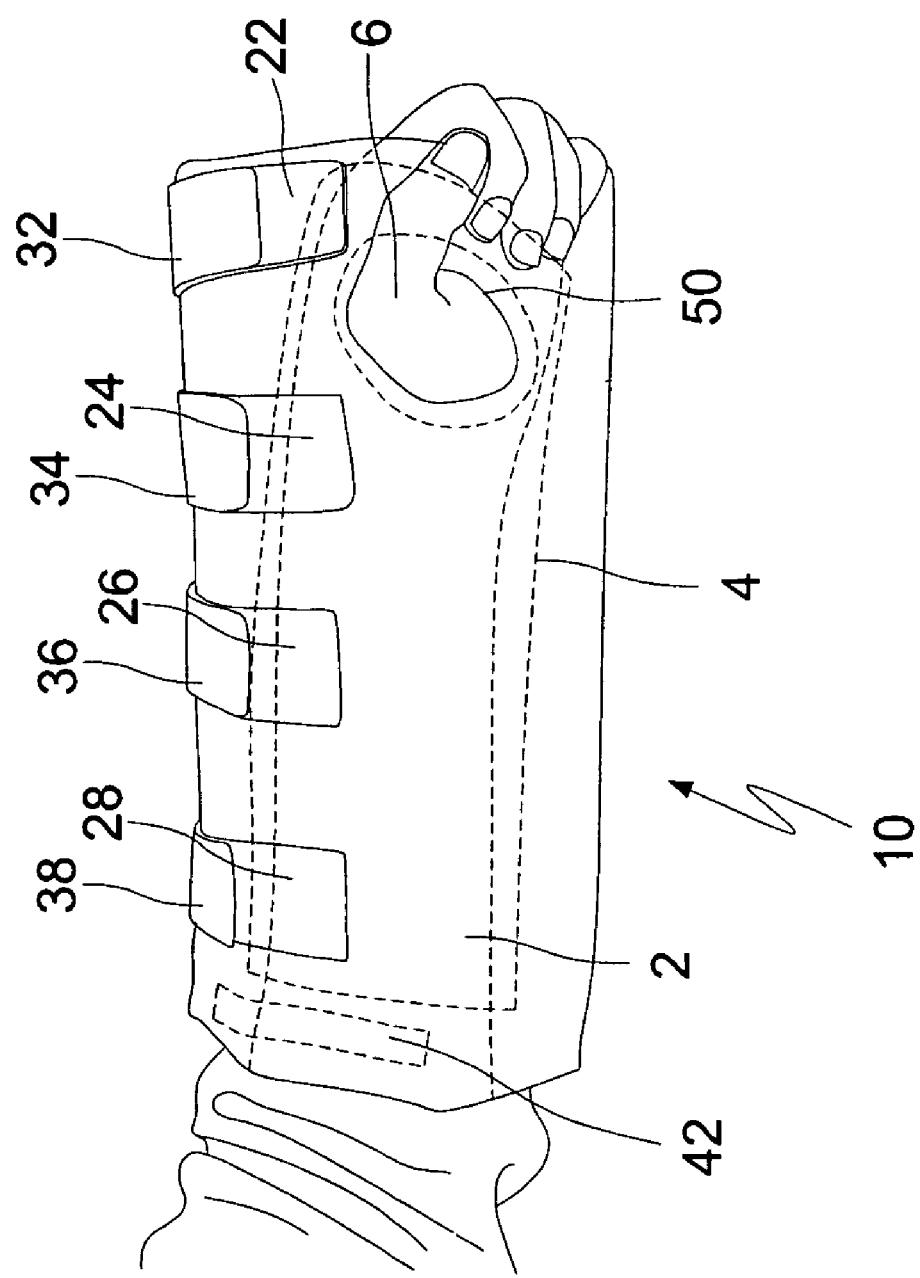
FIG. 3 is a perspective view of an exemplary cast cover.
Figure 6:
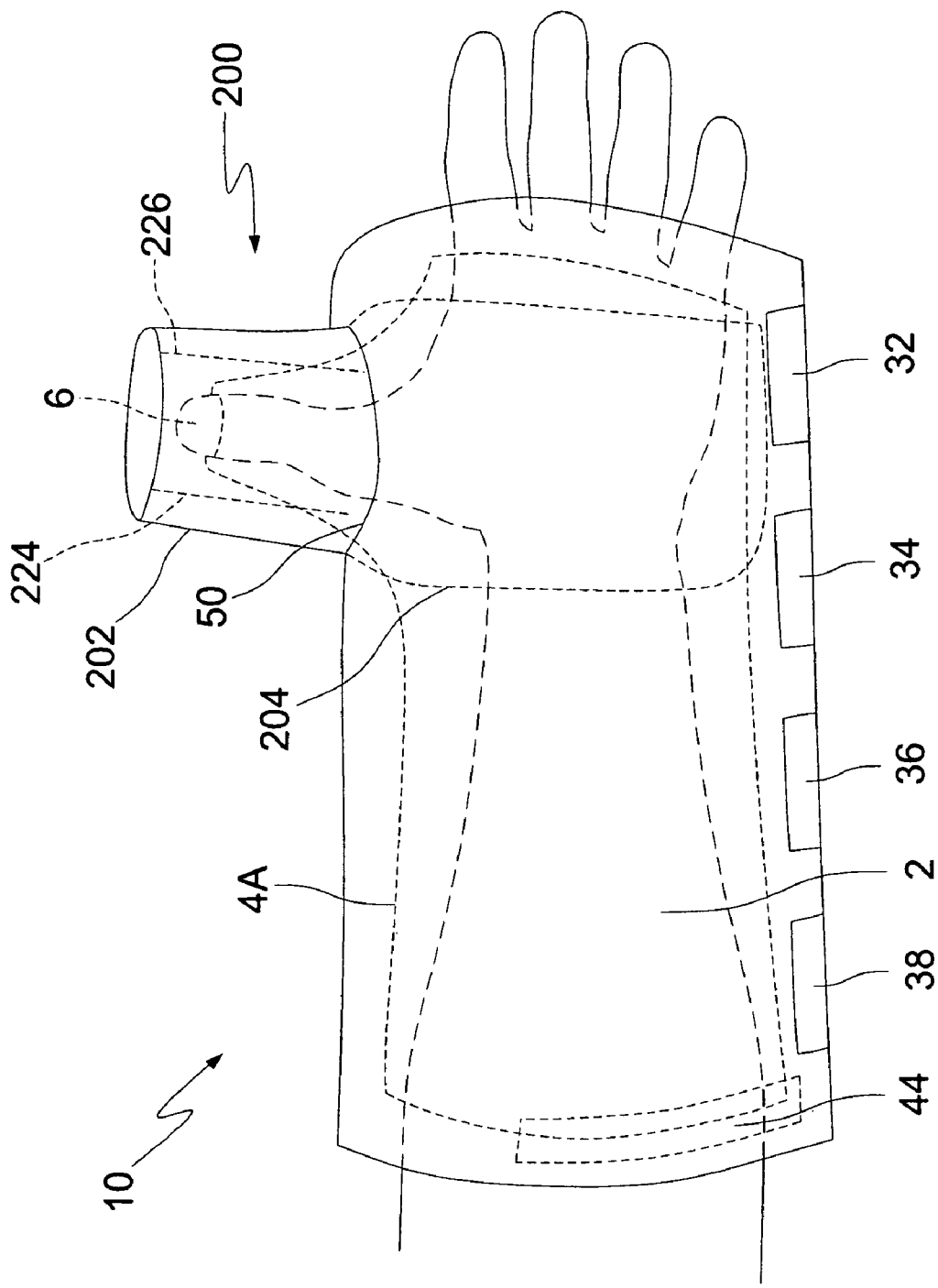
FIG. 6 is a perspective view of the exemplary thumb cover of FIG. 4 with an exemplary cast cover.
Figure 9:
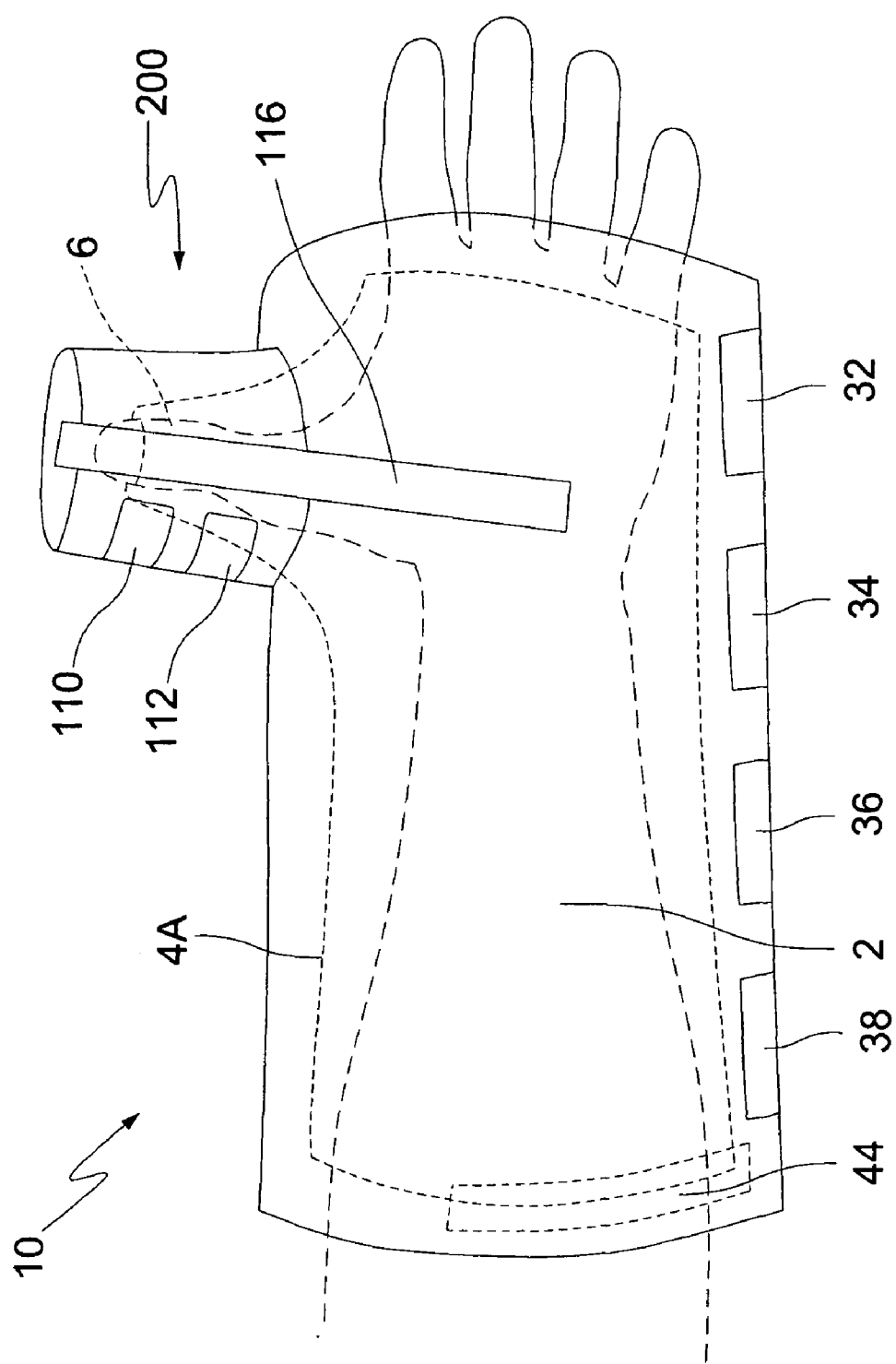
FIG. 9 is a perspective view of the exemplary thumb cover of FIG. 7 with an exemplary cast cover.

In an exemplary embodiment, the shell 20 may include features adapted to secure the cast cover 10 around a cast. In an exemplary embodiment, shell 20 includes four sets of hook and loop fasteners. The loop portions 22, 24, 26, 28 are sewn to the shell 20. Hook portions 32, 34, 36, 38 are also sewn to shell 20, but each extends beyond shell 20 in the form of straps. Each of the hook portions 32, 34, 36, 38 corresponds to one of the loop portions 22, 24, 26, 28 such that the cast cover may be wrapped around a cast and secured by coupling the corresponding portions as shown in FIGS. 3, 6, and 9.

While an exemplary embodiment depicted in FIG. 1 includes four sets of hook and loop fasteners, it is within the scope of the invention to include more or fewer fasteners. Further, the fasteners may not extend beyond the shell 20 in some embodiments. In such an embodiment, the cast cover 10 may wrap around the cast and fasten to itself using the provided one or more fasteners. In addition, fasteners other than hook and loop fasteners (such as, but not limited to, one or more zippers, tie strings, etc.) may be used in place of or in addition to the hook and loop fasteners described above.

In an exemplary embodiment, the cast cover 10 may include a core 60 which is adapted to fit within the pocket of the shell 20. As shown in FIG. 2, the core 60 may include a hole 62 which corresponds to the opening 50 in the shell 20. The core 60 may comprise an elastically-deformable foam, for example. In an exemplary embodiment, the core comprises 0.5 inch thick high-density closed-cell polyurethane foam. The core 60 may include other materials in addition to or in place of foam such as, but not limited to, other padding materials (such as, but not limited to, other foams and/or gels) and/or semi-rigid materials such as plastic sheet material. It is within the scope of the invention to utilize a core 60 which has a non-uniform thickness. In such an embodiment, the core may thicker at locations where additional padding is desired and may be thinner or absent at other locations. Further, it is within the scope of the invention to utilize a core comprised of a plurality of pieces.

In an exemplary embodiment, the core 60 may be removed from the shell 20 via the opening edge 40. The shell 20 may be cleaned and the same or another core 60 may be installed in the shell 20 prior to its next use. The user may select from a variety of cores 60 having different properties such as thickness, rigidity, elasticity, and the like based on the desired use.

The cast cover 10 may be constructed so as to satisfy the requirements set by an athletic organization for padding which must be worn over a cast by participants in an athletic event. For example, an athletic organization may require 0.5 inches of padding around a cast worn by a participant in an athletic event. An exemplary embodiment of the present invention may include sufficient padding to meet this requirement.

In some embodiments, the shell 20 and/or the core 60 may be constructed of materials which are soft, lightweight, durable, and/or washable. In addition, the materials used for the shell and/or the core 60 may be resistant to damage from water, dirt, sand, etc. Further, the shell 20 and/or the core 60 may be washable and reusable or may be disposable. The shell 20 may be constructed of a material which provides some padding and the shell 20 may include portions that are thicker or thinner than other portions. The shell 20 may be constructed of an elastically-deformable material such that, for example, the shell may stretch to conform to the object over which it is applied.

In an exemplary embodiment, the shell 20 may be constructed from latex-free, 80% polyester, and 20% spandex (elastane) 18 oz. (18 oz. per square yard) fabric. The fabric may be 4.5 mm (0.192 inches) thick.

The shell 20 and/or the core 60 may be provided in a variety of sizes and shapes. The various sizes and shapes may be adapted to fit users of various sizes and also may be adapted to be used to cover casts of various types, sizes, and shapes which may be used to immobilize various parts of the body.

In an exemplary embodiment shown in FIG. 1, dimension A may be 5.5 inches, dimension B may be 12 inches, and dimension C may be 12 inches. In an exemplary embodiment, the core 60 is approximately 0.5 inches thick and the shell 20 is approximately 0.2 inches thick, totaling approximately 0.7 inches when the cover 10 is assembled. It is within the scope of the invention to vary one or more of these dimensions.

Figure 4:
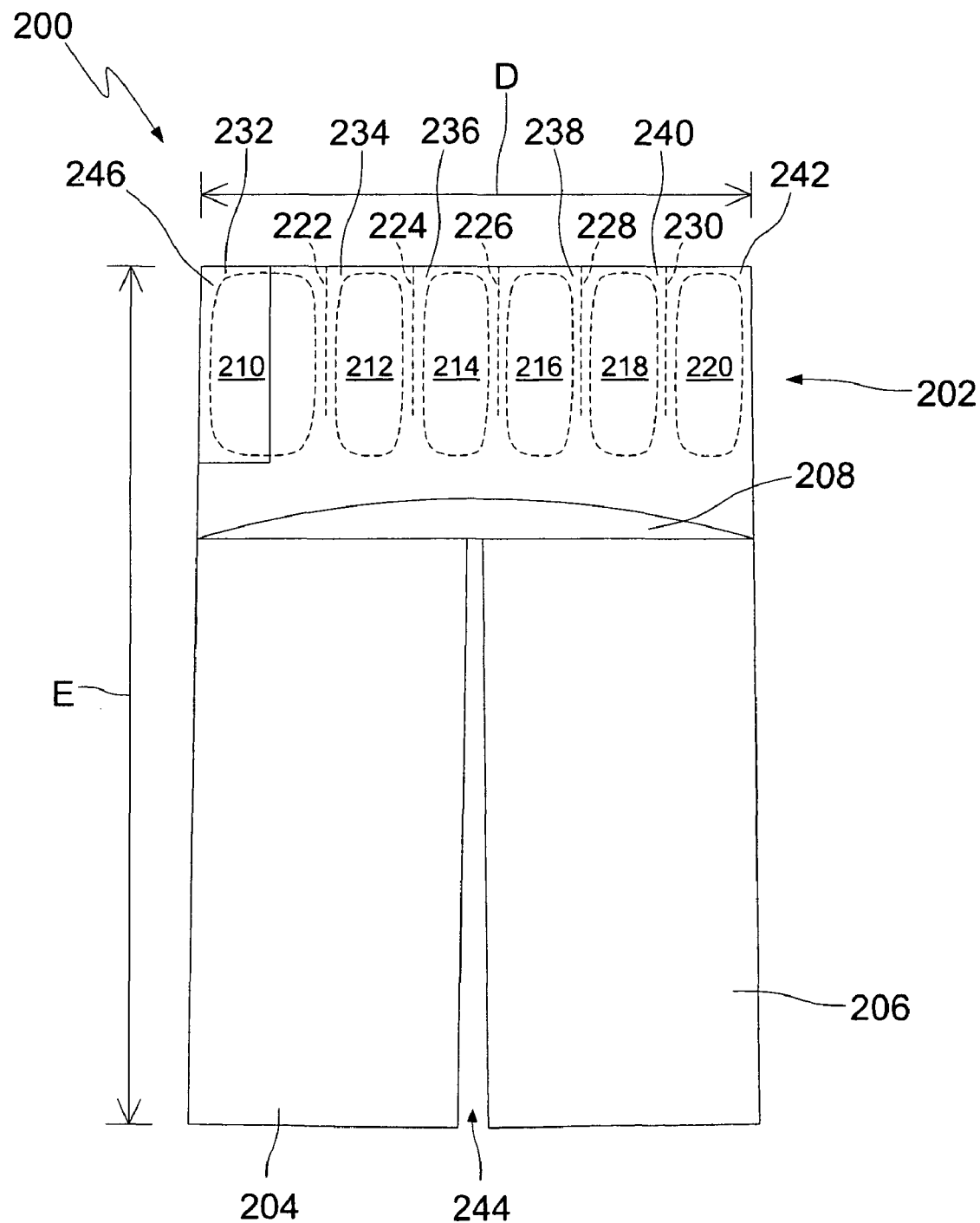
FIG. 4 is a plan view of one side of a thumb cover according to a first exemplary embodiment.
Figure 5:
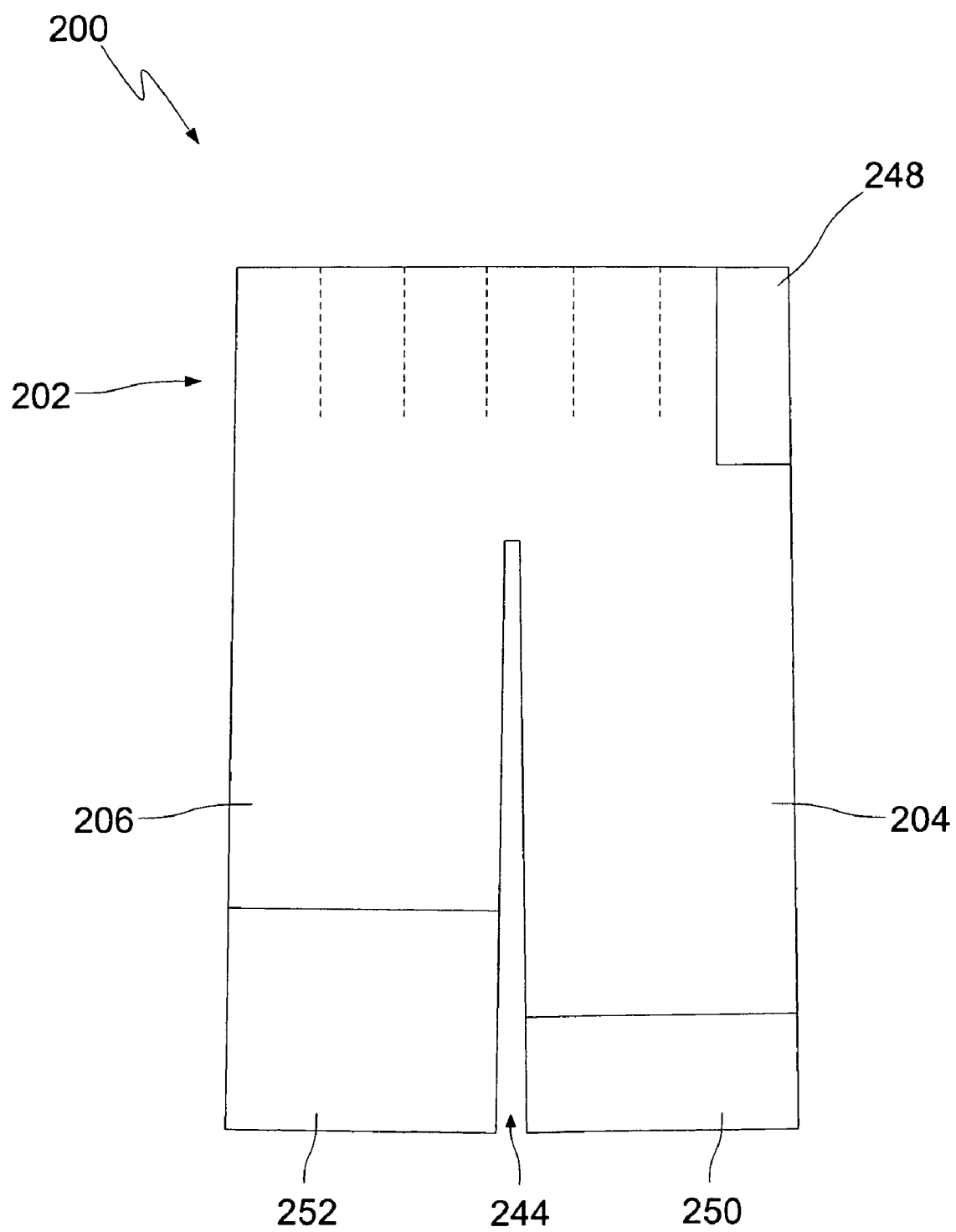
FIG. 5 is a plan view of the other side of the exemplary thumb cover of FIG. 4.
Figure 7:
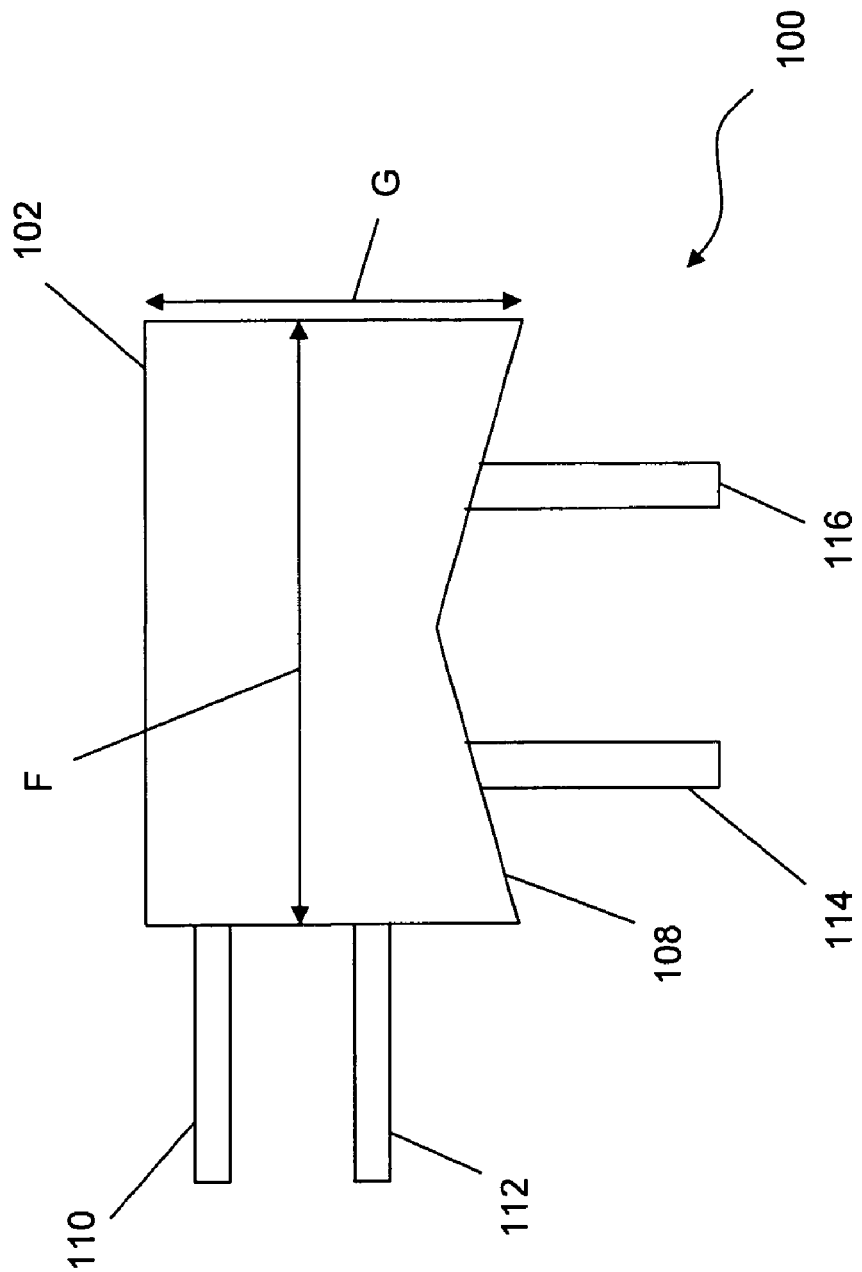
FIG. 7 is a plan view of an exemplary thumb cover according to a second exemplary embodiment.
Figure 8:
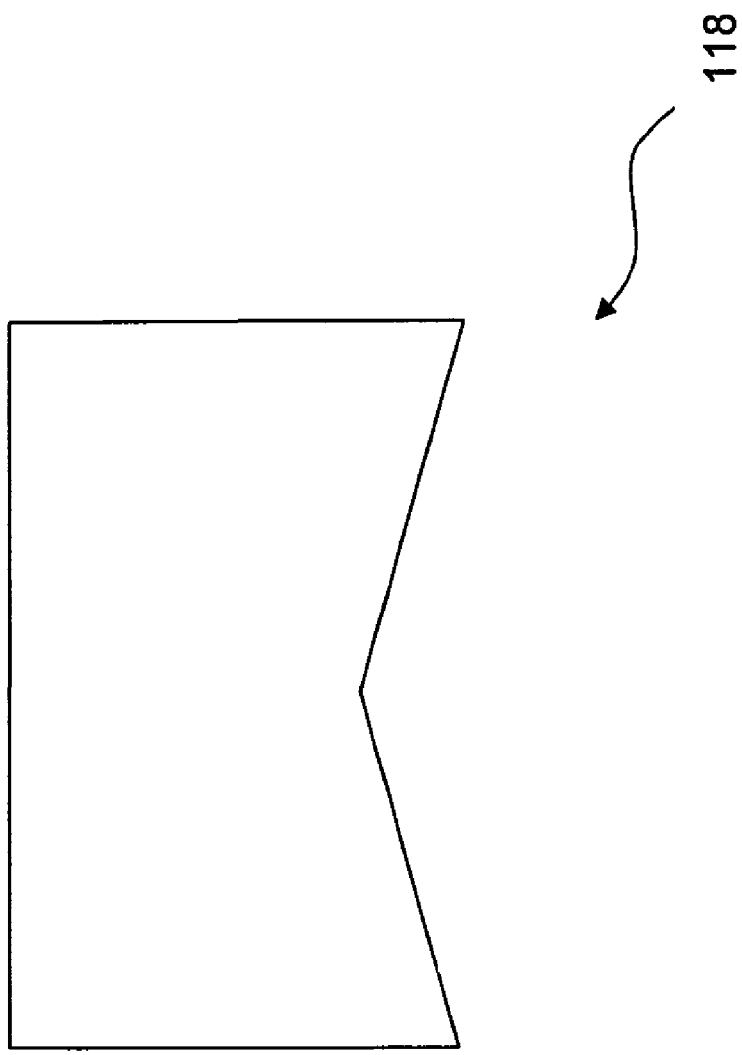
FIG. 8 is a plan view of an exemplary thumb cover core for use with the exemplary thumb pad of FIG. 7.

In some exemplary embodiments, cast cover 10 may include an additional padded portion, such as a thumb cover 100, 200. FIGS. 4-6 depict a first exemplary thumb cover 200, and FIGS. 7-9 depict a second exemplary thumb cover 100, which may be used, for example, when a cast 4A includes a portion around the thumb 6. In other embodiments, an additional padded portion may be adapted to cover other portions of a cast other than a thumb.

FIG. 4 depicts the "inside" of a first exemplary thumb cover 200, which includes a thumb-covering portion 202 and two flaps 204, 206. In the exemplary embodiment, the thumb-covering portion is constructed by folding a portion of fabric over itself and sewing the edges to create a space having an opening 208. The space may be divided into pockets 232, 234, 236, 238, 240, 242, which may be accomplished by sewing through the layers of fabric to create seams 222, 224, 226, 228, 230. One or more pads 210, 212, 214, 216, 218, 220 may be inserted into one or more of the pockets 232, 234, 236, 238, 240, 242. The pads 210, 212, 214, 216, 218, 220 may comprise any suitable padding material, such as elastically deformable foam.

The flaps 204, 206 may be formed by cutting the fabric to create a slot 244 between the flaps. One portion of a hook and look closure 246 is provided on the "inside" of the thumb pad 200. In an exemplary embodiment, dimension D may be approximately 7 inches, and dimension E may be approximately 11 inches.

Referring to FIG. 5, the "outside" of the thumb cover 200 may include the portion of the hook and loop closure 248 corresponding to closure 246, which may or may not be generally the same size. In addition, hook and loop closures 250, 252 may be provided on the flaps 204, 206.

As shown in FIG. 6, the exemplary thumb cover 200 may be utilized by wrapping the thumb covering portion 202 around a user's thumb 6 and securing the hook and loop closures 246, 248 to each other. The flaps 204, 206 are wrapped around the user's hand and/or wrist, and the hook and loop closures 250, 252 are secured to each other. Next, the cast cover 10 is placed on the user's arm and wrist such that the thumb cover 200 extends through opening 50. The cast cover 10 is secured using its hook portions 32, 34, 36, 38 and loop portions 22, 24, 26, 28.

FIGS. 7-9 depict a second exemplary embodiment thumb cover 100, which includes a thumb cover shell 102 and a thumb cover core 118. Thumb cover shell 102 and thumb cover core 118 may be constructed from the same materials as the shell 20 and core 60 or may be constructed of other materials having similar properties.

As shown in FIG. 7, the exemplary thumb cover 100 may be generally rectangular with a generally triangular cut out portion 108. Straps 110, 112, 114, 116 may be sewn to thumb cover shell 102. Straps 110, 112, 114, 116 may include hook and loop fasteners to attach to each other or to portions of thumb cover 100 or cast cover 10. Other means of attachment are within the scope of the disclosure. As shown in FIG. 8, thumb cover core 118 may have a similar shape and may be adapted to fit within thumb cover shell 102 in a manner similar to how core 60 fits within shell 20.

FIG. 9 depicts an exemplary embodiment of thumb cover 100 in use in conjunction with a cast cover 10. FIG. 9 shows the attachment locations for straps 110, 112, 116. As shown, the thumb cover 100 fits over the user's thumb that is extending through opening 50 in the shell 20. Straps 114, 116 extend around the around the user's wrist to affix thumb cover 100 to cast pad 10. In certain embodiments, straps 114, 116 extend fully around the user's wrist and may attach to each other. In other embodiments, straps 114, 116 may extend partially around the user's wrist and may join to corresponding hook and loop fastener portions on shell 20. It is within the scope of the invention to utilize other fastening devices. Further, it is within the scope of the invention for the thumb cover shell 102 to be sewn to the shell 20. Such an arrangement may obviate the need for one or more of straps 114, 116 or other fastening devices.

In the exemplary embodiment shown in FIG. 7, dimension F may be approximately 7 inches and dimension G may be approximately 4 inches. In an exemplary embodiment, the thumb cover core 118 is approximately 0.5 inches thick and the thumb pad shell 102 is approximately 0.2 inches thick, totaling approximately 0.7 inches when the thumb cover 100 is assembled. It is within the scope of the disclosure to vary one or more of these dimensions.

Exemplary thumb covers 100, 200 may be adapted to fit over the thumb portion of a cast. Thumb covers 100, 200 may be constructed as a hollow truncated cone, as a hollow cylinder having an angled end opening, or as any other shape suitable for covering the user's thumb and attaching to cast pad 10. Thumb covers 100, 200 may be provided in various sizes and shapes to accommodate users having different sizes of hands and wearing different casts.

It is within the scope of the disclosure to utilize the exemplary thumb covers 100, 200 without the cast pad 10 described above. Further, it is within the scope of the disclosure for an embodiment similar to the thumb covers 100, 200 to surround one or more body parts in addition to those within the a cast. For example, if a user's finger is immobilized with a cast (or, for example, a splint), an embodiment similar to the thumb covers 100, 200 may be adapted to surround the finger within the cast as well as one or more other fingers or the user's entire hand.

Although the exemplary embodiments described above have been set forth with reference to a cast, it is within the scope of the invention to utilize the present invention as a cover for any device which may be worn by a user and which may be covered. For example, embodiments of the present invention may be used to cover a splint worn by a user. Thus, as used herein, the term "cast" generally refers to any orthopedic immobilizing device, such as a plaster cast, a fiberglass cast, a splint, and the like.

While exemplary embodiments of the invention have been set forth above for the purpose of disclosure, modifications of the disclosed embodiments as well as other embodiments thereof may occur to those skilled in the art. Accordingly, it is to be understood that the disclosure contained herein are not limited to the above precise embodiments and that changes may be made without departing from the scope as defined by the claims. Likewise, it is to be understood that the scope is defined by the claims and it is not necessary to meet any or all of the stated advantages or objects invention disclosed herein to fall within the scope of the claims, since inherent and/or unforeseen advantages may exist even though they may not have been explicitly discussed herein.

What is claimed is:

1. A wearable article comprising:
a cast cover including
a substantially planar, resilient core including at least one opening extending therethrough,
a cast cover shell sized to receive the core and including at least one opening aligned with the opening in the core, and
at least one cast cover fastener coupled to the shell and arranged to retain the shell at least partially around an arm portion of a cast; and
a thumb cover including
a thumb cover shell including a plurality of thumb cover pockets,
a plurality of resilient thumb pads respectively received within the plurality of thumb cover pockets, and
at least one thumb cover fastener coupled to the thumb cover and arranged to retain the thumb cover at least partially around a thumb portion of the cast.

2. The article of claim 1, wherein the thumb cover includes two flaps arranged to extend around a wrist portion of the cast.

3. The article of claim 2, wherein the flaps include corresponding hook and loop closure portions arranged to couple the flaps together around the wrist portion of the cast.

4. The article of claim 1, wherein at least a portion of the thumb cover extends through the opening in the core and the opening in the arm cover shell.

5. The article of claim 1, wherein the at least one cast cover fastener includes a hook and loop fastener.

6. The article of claim 1, wherein the at least one thumb cover fastener includes a hook and loop fastener.

7. A protective cover for a cast comprising:
a core constructed of flexible and elastic foam sized to at least partially cover a cast;
an outer shell including a portion sized to receive the core such that the core is substantially covered by the shell;
a plurality of fasteners attached to the outer shell and arranged to retain the outer shell about the cast; and a thumb cover at least partially covering an extending thumb portion of the cast;
wherein the thumb cover includes a thumb cover shell and at least one thumb pad received with at least one pocket within the thumb cover shell.

8. A protective cover for a cast comprising:
a core constructed of flexible and elastic foam sized to at least partially cover a cast;

an outer shell including a portion sized to receive the core such that the core is substantially covered by the shell; and a plurality of fasteners attached to the outer shell and arranged to retain the outer shell about the cast; and wherein the outer shell includes a first opening and the core includes a second opening; and wherein the first opening and the second opening are aligned;

wherein the first opening and the second opening are positioned for a user's thumb to extend through.

9. The cover of claim 5, further comprising a thumb cover; wherein the thumb cover extends through the first opening and the second opening.

10. The cover of claim 8, wherein the core is completely enclosed by the outer shell.

11. A method for applying a protective cover for a cast, comprising:

arranging a cast cover at least partially around a cast, the cast cover including an outer shell, a resilient core received within the outer shell, and a cast cover fastener;

securing the cast cover in place around the cast by coupling the cast cover fastener; and installing a thumb cover over a thumb portion of the cast;

wherein the step of installing the thumb cover is performed prior to the step of arranging the cast cover around the cast; wherein the cast cover includes an opening; and wherein the step of arranging the cast cover around the cast includes placing the thumb cover through an the opening in the cast cover.

12. The method of claim 11, wherein the step of installing the thumb cover is performed after the step of arranging the cast cover around the cast; and wherein the step of installing the thumb cover includes affixing the thumb cover to the cast cover.

* * * * *